United States Patent [19]

Mardiguian

[11] 4,157,400
[45] * Jun. 5, 1979

[54] TERPENOPHENOXYALKYLAMINES AND PHARMACEUTICAL COMPOSITIONS AND USES THEREOF

[75] Inventor: Jean Mardiguian, Saint Maur des Fosses, France

[73] Assignee: MAR-PHA, Societe d'Etude et d'Exploitation de Marques, Paris, France

[ * ] Notice: The portion of the term of this patent subsequent to Dec. 6, 1994, has been disclaimed.

[21] Appl. No.: 822,726

[22] Filed: Aug. 8, 1977

[30] Foreign Application Priority Data

Aug. 10, 1976 [FR] France ................................ 76 24360

[51] Int. Cl.$^2$ ..................... A61K 31/135; C07C 93/06
[52] U.S. Cl. .................................. 424/330; 260/570.7
[58] Field of Search ...................... 424/330; 260/570.7

[56] References Cited

U.S. PATENT DOCUMENTS

| | | | |
|---|---|---|---|
| 3,551,493 | 12/1970 | Ruschig et al. | 424/330 |
| 3,836,671 | 9/1974 | Barrett et al. | 424/330 |
| 3,852,468 | 12/1974 | Howe et al. | 424/330 |
| 3,937,834 | 2/1976 | Hunger et al. | 424/330 |
| 4,061,777 | 12/1977 | Mardignian | 260/567.6 H |

*Primary Examiner*—Albert T. Meyers
*Assistant Examiner*—Douglas W. Robinson
*Attorney, Agent, or Firm*—Bucknam and Archer

[57] ABSTRACT

1-isopropylamino-3-[2-(2-norbornyl exo)phenoxy]propan-2-ol, its 1-isopropylamino-3-[2-norbornyl endo)-phenoxy]propan-2-ol isomer and their acid addition salts and their quaternary ammonium salts.

These compounds can be used as beta-blocking agents against disorders of the cardiac rhythm, anti-anxiety and anti-hypertension medicaments.

4 Claims, No Drawings

TERPENOPHENOXYALKYLAMINES AND PHARMACEUTICAL COMPOSITIONS AND USES THEREOF

The invention described in the Applicant's U.S. Pat. No. 4,061,777 relates to terpenophenoxyalkylamines of the general formula:

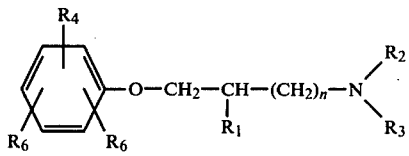

(I)

in which n=0, 1 or 2; $R_1$ is H, or a lower alkyl radical having a straight or branched chain with 1 to 4 carbon atoms, or an OH group; $R_2$ and $R_3$ each represent H or a lower alkyl radical having a straight or branched chain, with 1 to 4 carbon atoms, or a hydroxyethyl radical; $R_4$ is a terpene radical: 2-isobornyl (a), or 5-camphyl (b), or 2-norbornyl (c),

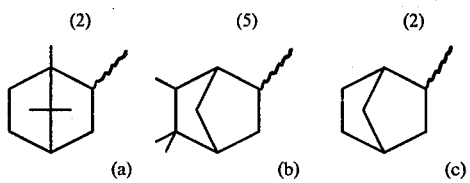

of exo or endo configuration, in the ortho, meta or para position with respect to the ether function; $R_5$ and $R_6$ each represent H or a lower alkyl radical having from 1 to 4 saturated or unsaturated carbon atoms, having a straight or branched chain, or a halogen atom: Cl, Br, I, F.

More particularly:
$R_1$ is H or OH
n is equal to 0 or 1
$R_2$ is a hydrogen atom,
$R_3$ is a hydrogen atom or isopropyl radical, or a hydroxy ethyl group —CH$_2$CH$_2$—OH
$R_5$, $R_6$ each represent a hydrogen atom or halogen atom, in particular Cl or Br, or a methyl radical, at position 4 or 5 of the phenol ring.

In particular, these amino-ethers have interesting bacteriostatic and bactericidal properties as regards gram+germs and gram−germs and can be used as anti-infectious agents. They also have vasodilatory and cardiovascular properties. They may be used in the form of physiologically acceptable non-toxic bases or acid salts, or in the form of quaternary ammonium salts.

It has now been found that 1-isopropylamino-3-[2-(2-norbornyl exo)phenoxy]propan-2-ol isomers of the formula:

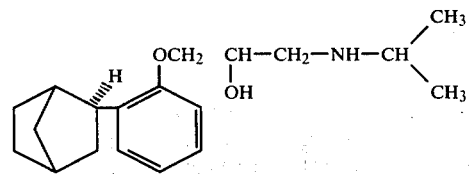

and 1-isopropylamino-3-[2-(2-norbornyl endo)phenoxy]propan-2-ol of formula:

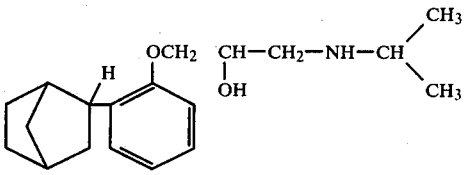

as well as their physiologically acceptable non-toxic acid addition salts, in particular their hydrochlorides and their quaternary ammonium salts have, in addition to the afore-mentioned properties for terpenophenoxyalkylamine compounds, a beta-blocking or beta-sympatholytic activity over a prolonged period of time.

The present invention therefore relates to terpenophenoxyalkylamines chosen from the group comprising the isomers:

1-isopropylamino-3-[2-(2-norbornyl exo)phenoxy]propan-2-ol and 1-isopropylamino-3-[2-(2-norbornyl endo)phenoxy]propan-2-ol, their physiologically acceptable non-toxic acid addition salts and their quaternary ammonium salts.

The invention also relates to a medicament which can be used as a beta-blocking agent against disorders of the cardiac rhythm, as anti-anxiety, anti-hypertension and anti-spasmodic medicaments, containing at least one terpenophenoxyalkylamine defined above.

The invention also relates to a pharmaceutical composition containing, as the active ingredient, at least one terpenophenoxyalkylamine defined above, associated, in a physiologically active quantity, with a pharmaceutically acceptable non-toxic support.

These new terpenophenoxyalkylamines may be prepared by condensation of a 2-(2-norbornyl exo or endo) phenate of alkaline metal with an epihalohydrin, preferably epichlorohydrin, to form the derivative 2-(2-norbornyl exo or endo)-1-phenoxy-2,3-epoxypropane and reaction of the latter to form the desired product which is isolated and possibly transformed into an acid addition salt or quaternary ammonium salt in manner known per se.

The invention is illustrated by the following non-limiting examples:

EXAMPLE 1

1-isopropylamino-3-[2-(2-norbornyl exo)phenoxy]propan-2-ol 24.5 g (0.13 mole) 2-(2-norbornyl exo) phenol (L. A. KHEIFITS and A. E. GOL'DOVSKII, Zh. Obshch. Khim., 1963, 33, 2048.), 350 cm$^3$ anhydrous toluene and 3 g (0.13 mole) metallic sodium are introduced into a three-neck flask through which a stream of nitrogen flows.

The reaction mixture is refluxed until the liberation of hydrogen ceases, then the solvent is driven off under reduced pressure and the residue is taken up in 250 cm$^3$ tetrahydrofuran. 24 g (0.26 mole) epichlorohydrin are then added and the mixture is heated under reflux for 6 hours. An extraction with ether is then undertaken, the organic phase is washed with water, dried and the solvent is evaporated. 25 g 2-(2-norbornyl exo)-1-phenoxy-2,3-epoxypropane are thus obtained in the form of an oil.

15 g (0.06 mole) of the preceding product are dissolved in 50 cm$^3$ isopropylamine. After 4 days contact, the excess amine is evaporated under reduced pressure, then an extraction with ether is carried out. After washing with water and drying, the ethereal phase is saturated with gaseous hydrochloric acid.

The precipitate formed is washed abundantly with ether then crystallised from an acetone/ethanol mixture (3/2). 16 g of the desired product in the form of the hydrochloride are thus obtained, having a melting point of 189°–191° C.

ANALYTICAL CHARACTERISTICS

Analysis for $C_{19}H_{30}ClNO_2$ ( molecular weight 339)

|  | C % | H % | N % |
|---|---|---|---|
| Calculated | 67.25 | 8.84 | 4.12 |
| Found | 67.20 | 8.82 | 3.83 |

INFRARED SPECTRUM

In dispersion in KBr, the characteristic bands are as follows:

| | | |
|---|---|---|
| $\overset{\oplus}{-NH_2}$ | $2795\ cm^{-1}$, | $1585\ cm^{-1}$ |
| —OH | $3300\ cm^{-1}$ | |
| - aromatic cycle 1600, 1500, 750 $cm^{-1}$ | | |
| - ether linkage 1245 $cm^{-1}$, 1045 $cm^{-1}$ | | |

NUCLEAR MAGNETIC RESONANCE

In solution in D.M.S.O. $d_6$ (deuterated dimethylsulphoxide), the following are noted with respect to H.M.D.S.
Norbornyl 1.3 ppm
Isopropyl methyls 1.2 ppm (doublet)
Methine 4.2 ppm
Aromatic protons 6.9 ppm.

EXAMPLE 2

1-isopropylamino-2-(2-norbornyl endo)-3-phenoxy-propan-2-ol 200 cm³ anhydrous toluene and 3.45 g (0.15 mole) metallic sodium are introduced into a 1 liter three-neck flask, through which a stream of nitrogen flows. The mixture is heated under reflux, with vigorous stirring, then 28.24 g (0.15 mole) 2-(2-norbornyl endo)phenol (L. A. KHEIFITS, A. E. GOL'DOVSKII J. Org. Chem. U.S.S.R. 1969, 5, (10), 1745–1748). are then added slowly. At the end of this addition, heat is applied for 1 hour, then the solvent is driven off under reduced pressure and the residue is taken up in 200 cm³ tetrahydrofuran. 27.75 g (0.3 mole) epichlorohydrin are then added and one heats under reflux for 3 hours. The solvent is eliminated by evaporation and the residue is taken up in ether, the insoluble material is filtered over "celite" and the organic phase is washed abundantly with water. The ethereal layer is dried and the ether is eliminated by evaporation in order to obtain 32 g 2-(2-norbornyl endo)-1-phenoxy-2,3-epoxypropane, in the form of an oil.

15 g (0.06 mole) of the latter product are then dissolved in 50 cm³ isopropylamine and the resulting solution is left for 3 days at ambient temperature. The excess amine is evaporated under reduced pressure, then an extraction with ether is carried out. The ethereal phase after washing with water and drying, is then saturated with gaseous hydrochloric acid. The precipitate thus formed, crystallised from acetone, gives 9.3 g of the desired product, in the form of the hydrochloride having a melting point of 162°–164° C.

ANALYTICAL CHARACTERISTICS

Analysis for $C_{19}H_{30}ClNO_2$ (molecular weight 339)

|  | C % | H % | N % |
|---|---|---|---|
| Calculated | 67.25 | 8.84 | 4.12 |
| Found | 67.26 | 8.84 | 3.93 |

INFRARED SPECTRUM

In dispersion in KBr the characteristic bands are as follows:

| | | |
|---|---|---|
| $\overset{\oplus}{-NH_2}$ | $2795\ cm^{-1}$, | $1560\ cm^{-1}$ |
| —OH | $3300\ cm^{-1}$ | |
| - aromatic cycle 1600, 1500, 755 $cm^{-1}$ | | |
| - ether linkage 1250 $cm^{-1}$, 1060 $cm^{-1}$ | | |

NUCLEAR MAGNETIC RESONANCE

In solution in deuterated chloroform, the following are noted with respect to TMS
norbornyl 1.3 ppm
isopropyl methyls 1.45 ppm (doublet)
methine 4.6 ppm
aromatic protons 7 ppm.

TOXICOLOGICAL PROPERTIES

Acute toxicities of the compounds according to the invention have been determined in the male mouse CD1 (Charles RIVER) both intravenously and orally. The LD50 were calculated after observation for 3 days by the method of REED, JJ. and MUENCH, H. (Am. J. Hy, 27 493, 1938).

The LD50 obtained are summarised in the following table:

| No. of example | Acute toxicity in the mouse | |
|---|---|---|
| | LD50 | mg/kg |
| | Intravenously | Orally |
| 1 | 60 | 800 |
| 2 | 62 | 675 |

The two compounds behave as substances which are only relatively slightly toxic in the mouse.

PHARMACOLOGICAL PROPERTIES 1.beta-sympatholytic properties

The beta-sympatholytic properties of the two compounds of the invention have been demonstrated in a non-anesthetized rabbit intravenously and orally.

The technique consists of evaluating the antagonism exerted by the products with regard to induced tachycardia, in an alert rabbit, by a sympatho-stimulant agent, isoproterenol, administered in a dose of 0.010 mg/kg intravenously. The animal is placed in a restraining box and the marginal vein of the ear is catheterized. The animal's electrocardiogram is picked up by two electrodes implanted in shunt DII and connected to a telemetric transmitter. A polygraph, coupled to a receiver, simultaneously records the electrocardiogram and the cardiac rhythm by integration of the waves R.

First of all, one makes certain of the stability and reproducibility of isoprenalinic tachycardia and the substance to be studied is administered. In the case of intravenous administration of the products, the injections of isoproterenol are then repeated 5 minutes later, then every 15 minutes, until the tachycardia returns to its initial intensity. When the products are administered orally, the injections of the beta-stimulant are repeated 15, 30, 45 and 60 minutes, then 2, 3, 5, 24 and 48 hours afterwards.

The beta-sympatholytic activity is expressed by the maximum percentage decrease of the tachycardia induced by isoproterenol. The total duration of the effect is also noted.

The following tables summarise the results obtained with the products according to the invention:

A-Intravenous administration

| Ex. | Intravenous dose mg/kg | Maximum Inhibition of tachycardia (as a %) | Duration of Inhibiting effect |
|---|---|---|---|
| 1 | 0.1 | 24 | approx. 50 minutes |
|   | 0.3 | 67 | approx 2½ hours |
|   | 0.5 | 54 | more than 2 hrs. |
|   | 1   | 86 | more than 2 hrs. |
| 2 | 0.5 | 20 | approx. 40 mins. |
|   | 1   | 67 | approx. 4 hrs. |

B-Oral Administration

| Example | Oral dose mg/kg | Maximum Inhibition of tachycardia (as a %) | Duration of Inhibiting effect |
|---|---|---|---|
| 1 | 9 | 40 | more than 3 hrs. |
|   | 17.5 | 73 | approx. 24 hrs. |
|   | 35 | 88 | approx. 48 hrs. |
|   | 75 | 80 | approx. 48 hrs. |
|   | 150 | 82 | more than 48 hrs. |
| 2 | 17.5 | 64 | approx. 24 hrs. |
|   | 35 | 60 | approx. 48 hrs. |
|   | 75 | 80 | approx. 48 hrs. |
|   | 150 | 81 | approx. 48 hrs. |

The two products of the invention therefore exert powerful beta-sympatholytic effects, which last for a surprisingly long time when administered both intravenously as well as orally.

2. Coronaro-dilatory activities

The coronaro-dilatory activities of the compounds of the invention have been demonstrated on a rabbit's heart in a technique derived from that of LANGENDORFF, (Arch. Ges. Physiol., 61, 201, 1895). In this technique, the survival liquid perfusing the heart contains 0.5 I.U./l post-hypophysis intended for permanently maintaining a slight vaso-constriction of the coronary vascular system. The products to be studied are administered in the region of the aortic canal in a volume of 1 cm$^3$ over a period of 1 minute. The results are expressed as a percentage variation of the coronary output after the injection of the product with respect to the initial output, the output being measured by integration of the frequency of drops of survival liquid escaping from the heart after having passed through the coronary system.

The results obtained with the product of Example 1 are given in the following table:

| Dose in mg/l | % Variation of coronary output | Duration of the effect in mins. |
|---|---|---|
| 0.003 | + 13 | 3 |
| 0.010 | + 57 | 3 |
| 0.030 | + 133 | 15 |

-continued

| Dose in mg/l | % Variation of coronary output | Duration of the effect in mins. |
|---|---|---|
| 0.100 | + 225 | 9 |

The product of Example 1 exerts considerable coronaro-dilatory effects, whose intensity and duration clearly increase with the concentration.

3. Spasmolytic activity

The spasmolytic activities of the compounds of the invention have been demonstrated by means of the technique of MAGNUS R. (Arch. Ges. Physiol., 102, 123, 1904) on the removed duodenum of the rat. The spasmolytic neurotropes inhibit the contractions of the organ caused by acetylcholine, whereas the musculotropes prevent the spasms induced by barium chloride. The following table summarises the results expressed as a 50% effective concentration (EC50) in mg/l.

| | Spasmolytic activities on the detached duodenum of the rat (EC50) mg/l | |
|---|---|---|
| Example | Neurotrope (versus acetylcholine) | Musculotrope (versus BaCl$_2$) |
| 1 | 0.18 | 0.15 |
| 2 | 0.30 | 0.04 |

The two products of the invention have powerful spasmolytic properties, both neurotropic and musculotropic.

THERAPEUTIC USE

In view of their considerable and lasting beta-adrenolytic activities, associated with vasodilatory and spasmolytic properties, the products of the invention may be used to treat humans in all fields of application of beta-sympatholytic substances, in particular against various disorders of the cardiac rhythm and as anti-anxiety and anti-hypertension substances for example. They may also be used as anti-spasmodic substances.

The compounds according to the invention and their pharmaceutically acceptable salts may be administered in the form of tablets, sugar coated pills, capsules, cachets, suppositories, injectable ampoules, drinkable liquids etc. in unitary doses comprised, according to the galenic forms and compounds, between 10 and 200 mg according to a daily dosage which can vary from 20 to 1200 mg.

What is claimed is:

1. A compound selected from the group consisting of 1-isopropylamino-3-[2-(2-norbornyl exo)phenoxy]propan-2-ol, its isomer: 1-isopropylamino-3-[2-(2-norbornyl endo)phenoxy]propan-2-ol, and physiologically acceptable non-toxic acid addition salts and quaternary ammonium salts thereof.

2. A pharmaceutical composition active as a beta-blocking agent against tachycardia, as an anti-anxiety, anti-hypertension and anti-spasmodic medicament which comprises a therapeutically effective amount of at least one compound according to claim 1, and a pharmaceutically acceptable non-toxic carrier.

3. A method for the treatment of tachycardia, of angina pectoris and hypertension which comprises administering orally or intravenously to a patient in need of such treatment a composition containing as the active ingredient a compound which is 1-isopropylamino-3-[2-(2-norbornyl exo)phenoxy]propan-2-ol) or its isomer: 1-isopropylamino-3-[2-(2-norbornyl endo)phenoxy]propan-2-ol to the patient in a daily dose of 20 to 1200 mg. of said compound.

4. Pharmaceutical composition according to claim 2 in the form of a tablet, sugar coated pill, capsule, cachet, suppository, injectable ampoules or drinkable liquid containing between 10 and 200 mg. of said compound per unit dose.

* * * * *